United States Patent
Kumar et al.

(10) Patent No.: US 9,916,313 B2
(45) Date of Patent: **\*Mar. 13, 2018**

(54) MAPPING OF EXTENSIBLE DATASETS TO RELATIONAL DATABASE SCHEMAS

(71) Applicants: Srinivasan Kumar, Sunnyvale, CA (US); Anja Bog, Mountain View, CA (US); Kannan Avudai, Santa Clara, CA (US); Enakshi Singh, San Francisco, CA (US)

(72) Inventors: Srinivasan Kumar, Sunnyvale, CA (US); Anja Bog, Mountain View, CA (US); Kannan Avudai, Santa Clara, CA (US); Enakshi Singh, San Francisco, CA (US)

(73) Assignee: SAP SE, Walldorf (DE)

( \* ) Notice: Subject to any disclaimer, the term of this patent is extended or adjusted under 35 U.S.C. 154(b) by 551 days.

This patent is subject to a terminal disclaimer.

(21) Appl. No.: 14/339,391

(22) Filed: Jul. 23, 2014

(65) Prior Publication Data

US 2015/0234842 A1    Aug. 20, 2015

Related U.S. Application Data

(60) Provisional application No. 61/940,198, filed on Feb. 14, 2014.

(51) Int. Cl.
*G06F 7/00* (2006.01)
*G06F 17/30* (2006.01)
(Continued)

(52) U.S. Cl.
CPC .... *G06F 17/30091* (2013.01); *G06F 17/3012* (2013.01); *G06F 17/30292* (2013.01);
(Continued)

(58) Field of Classification Search
CPC ......... G06F 17/30091; G06F 17/30339; G06F 17/30292; G06F 17/3012; G06F 17/30315;
(Continued)

(56) References Cited

U.S. PATENT DOCUMENTS 6,035,303 A * 3/2000 Baer ................. G06F 17/30607
7,426,734 B2    9/2008 Debique et al.
(Continued)

OTHER PUBLICATIONS

"Import variants, genotypes and related information fields" Nov. 23, 2013 https://web.archive.org/web/20131123185331/http://variant-tools.sourceforge.net/Vtools/Import.*

*Primary Examiner* — Kannan Shanmugasundaram
(74) *Attorney, Agent, or Firm* — Mintz Levin Cohn Ferris Glovsky and Popeo, P.C.

(57) ABSTRACT

Data including a text file is received. The text file is arranged in an extensible format and includes a plurality of metadata lines, a header line, and a plurality of content lines. Metadata from the metadata lines is mapped to a plurality of metadata tables in a database that are formed according to a relational database schema using prefix parameters from each metadata line. Content from the content lines is mapped to a plurality of content tables in the database that are formed according to the relational database schema using the header line. A first subset of the content tables have a static structure and a second subset of the content tables have a dynamic structure. Related apparatus, systems, techniques and articles are also described.

21 Claims, 11 Drawing Sheets

(51) Int. Cl.
*G06F 19/28* (2011.01)
*G06F 19/00* (2018.01)
*G06F 17/00* (2006.01)

(52) U.S. Cl.
CPC .. *G06F 17/30315* (2013.01); *G06F 17/30339* (2013.01); *G06F 17/30864* (2013.01); *G06F 17/30917* (2013.01); *G06F 17/30952* (2013.01); *G06F 17/30997* (2013.01); *G06F 19/28* (2013.01); *G06F 19/70* (2013.01)

(58) Field of Classification Search
CPC ......... G06F 17/30864; G06F 17/30917; G06F 17/30997
USPC ........................................................ 707/741
See application file for complete search history.

(56) References Cited

U.S. PATENT DOCUMENTS

| | | |
|---|---|---|
| 8,954,461 B2 | 2/2015 | Ware et al. |
| 2005/0283374 A1 | 12/2005 | Salomon et al. |
| 2011/0004622 A1* | 1/2011 | Marson ................. G06Q 10/06 707/770 |
| 2012/0102451 A1 | 4/2012 | Kulkarni et al. |
| 2012/0231959 A1* | 9/2012 | Elton ..................... G06Q 50/22 506/2 |
| 2013/0086118 A1 | 4/2013 | Ware et al. |
| 2013/0144896 A1 | 6/2013 | Kim |
| 2013/0179962 A1 | 7/2013 | Arai et al. |
| 2015/0234870 A1 | 8/2015 | Kumar et al. |

\* cited by examiner

400

```
##fileformat=VCFv4.2
##fileDate=20090805
##source=myImputationProgramV3.1
##reference=file:///seq/references/1000GenomesPilot-NCBI36.fasta
##contig=<ID=20,length=62435964,assembly=B36,md5=f126cdf8a6e0c7f379d618ff66beb2da,species="Homo sapiens",taxonomy=x>
##phasing=partial
##INFO=<ID=AC,Number=A,Type=Integer,Description="Allele count in genotypes, for each ALT allele, in the same order as listed",Version="1.0",Source="Anja">
##INFO=<ID=AF,Number=A,Type=Float,Description="Allele Frequency, for each ALT allele, in the same order as listed">
##INFO=<ID=AN,Number=1,Type=Integer,Description="Total number of alleles in called genotypes">
##INFO=<ID=BaseQ,Number=1,Type=Float,Description="Z-score from Wilcoxon rank sum test of Alt Vs. Ref base qualities">
##INFO=<ID=DB,Number=0,Type=Flag,Description="dbSNP Membership">
##FILTER=<ID=BGL, Description="This 'T' site was set to monomorphic by Beagle">
##FILTER=<ID=Tr99,Description="Truth sensitivity tranche level at VSQ Lod: -2.0669 <= x < 2.6677">
##FORMAT=<ID=AD,Number=,,Type=Integer,Description="Allelic depths for the ref and alt alleles in the order listed">
##FORMAT=<ID=DP,Number=1,Type=Integer,Description="Read Depth (only filtered reads used for calling)">
##FORMAT=<ID=GQ,Number=1,Type=Float,Description="Genotype Quality">
##FORMAT=<ID=GT,Number=1,Type=String,Description="Genotype">
##FORMAT=<ID=OG,Number=1,Type=String,Description="Original Genotype input to Beagle">
##FORMAT=<ID=PL,Number=G,Type=Integer,Description="Normalized, Phred-scaled likelihoods for genotypes as defined in the VCF specification">
```

410 — header lines above

| #CHROM | POS | ID | REF | ALT | QUAL | FILTER | INFO | FORMAT | NA00001 | NA00002 | NA00003 |
|---|---|---|---|---|---|---|---|---|---|---|---|
| chr22 | 16053241 | . | C | T | 33 | PASS | AC=3;AF=0.03;AN=94;BaseQ=0.9 | GT:AD:DP:GQ:OG:PL | 0|0:2,0:2:50:..:0,6,73 | 0|0:3,0:3:22,29:..:0,9,9 | 0|0:3,0:3:35,23:..:0,9,82 |
| chr22 | 16053248 | . | T | C | 572 | BGl, Tr99 | AC=12;AF=0.12;AN=94;BaseQ=-2.8 | GT:AD:DP:GQ:OG:PL | 0|0:2,0:2:50:..:0,3,38 | 0|0:4,0:4:10,96:..:0,9,9 | 0|0:4,0:4:10,96:..:0,9,82 |
| chr22 | 16053444 | Rs80167676 | A | T,GAAATGTA | 469 | PASS | AC=4;AF=0.04;AN=94;BaseQ=-0.9;DB | GT:AD:DP:GQ:OG:PL | 0|0:4,0:4:30:..:0,12,144 | 0|0:4,0:4:36,99:..:0,9,1 | 1|2:4,0:4:40:..:0,12,138 |
| chr22 | 16053791 | Rs11703994 | C | A | 733 | Tr99 | AC=16;AF=0.17;AN=94;BaseQ=-1.3;DB | GT:AD:DP:GQ:OG:PL | 0|0:4,0:4:60:..:0,9,92 | 0|0:2,0:2:7,53:..:0,6,67 | 1|0:1,1:2:20,92:..:2,0,22 |
| chr22 | 16053814 | Rs113763510 | C | T | 217 | PASS | AC=6;AF=0.064;AN=94;BaseQ=1.0;DB | GT:AD:DP:GQ:OG:PL | 0|0:3,0:3:28,54:..:0,9,92 | 0|0:..:..:29,59:./.. | 0|0:3,0:3:40:..:0,9,83 |

420 — header row; 430 — data rows

VARIANT_SOURCE_MASTER / 510

| DATA_SET | ATTRIBUTE_NAME | ATTRIBUTE_VALUE | ETL_LOAD_ID |
|---|---|---|---|
| e.g. 1 | fileformat | VCFv4.2 | 1 |
| e.g. 1 | fileDate | 20090805 | 1 |
| e.g. 1 | source | myImputationProgramV3.1 | 1 |
| e.g. 1 | reference | file:///seq/references/1000GenomesPilot-NCBI36.fasta | 1 |
| e.g. 1 | phasing | partial | 1 |

VARIANT_CONTIG_MASTER / 530

| DATA_SET | CONTIG_ID | NAME | VALUE | ETL_LOAD_ID |
|---|---|---|---|---|
| e.g. 1 | 20 | length | 62435964 | 1 |
| e.g. 1 | 20 | assembly | B36 | 1 |
| e.g. 1 | 20 | md5 | f126cdf8a6e0c7f379d618ff66beb2da | 1 |
| e.g. 1 | 20 | species | Homo sapiens | 1 |
| e.g. 1 | 20 | taxonomy | x | 1 |

/ 410

```
1  ##fileformat=VCFv4.2
2  ##fileDate=20090805
3  ##source=myImputationProgramV3.1
4  ##reference=file:///seq/references/1000GenomesPilot-NCBI36.fasta
5  ##contig=<ID=20,length=62435964,assembly=B36,md5=f126cdf8a6e0c7f379d618ff66beb
   2da,species="Homo sapiens",taxonomy=x>
6  ##phasing=partial
7  ##INFO=<ID=AC,Number=A,Type=Integer,Description="Allele count
   ..",Version="1.0",Source="Anja">
8  ##INFO=<ID=AF,Number=A,Type=Float,Description="Allele Frequency...">
9  ##INFO=<ID=AN,Number=1,Type=Integer,Description="Total number of alleles...">
10 ##INFO=<ID=BaseQ,Number=1,Type=Float,Description="Z-score from Wilcoxon rank s...">
11 ##INFO=<ID=DB,Number=0,Type=Flag,Description="dbSNP Membership">
12 ##FILTER=<ID=BGL,Description="site set to monomorphic by Beagle">
13 ##FILTER=<ID=Tr99,Description="Truth sensitivity VSQ Lod: -2.067 <= x < 2.67">
14 ##FORMAT=<ID=AD,Number=,Type=Integer,Description="Allelic depths...">
15 ##FORMAT=<ID=DP,Number=1,Type=Integer,Description="Read Depth...">
16 ##FORMAT=<ID=GQ,Number=1,Type=Float,Description="Genotype Quality">
17 ##FORMAT=<ID=GT,Number=1,Type=String,Description="Genotype">
18 ##FORMAT=<ID=OG,Number=1,Type=String,Description="Orig Genotype input..">
19 ##FORMAT=<ID=PL,Number=G,Type=Integer,Description="Normalized, Phred-scaled...">
```

VARIANT_INFO_MASTER / 520

| DATA_SET | DATA_TYPE | INFO_ID | NUMBER | DESCRIPTION | ETL_LOAD_ID |
|---|---|---|---|---|---|
| e.g. 1 | Integer | AC | A | Allele count .. | 1 |
| e.g. 1 | Float | AF | A | Allele Frequency.. | 1 |
| e.g. 1 | Integer | AN | 1 | Total number of alleles.. | 1 |
| e.g. 1 | Float | BaseQ | 1 | Z-score from Wilcoxon rank s.. | 1 |
| e.g. 1 | Flag | DB | 0 | dbSNP Membership | 1 |

VARIANT_FILTER_MASTER / 540

| DATA_SET | DESCRIPTION | FILTER_ID | ETL_LOAD_ID |
|---|---|---|---|
| e.g. 1 | T site set to monomorphic by Beagle | BGL | 1 |
| e.g. 1 | Truth s.. VSQ Lod: -2.067 <= x < 2.67 | Tr99 | 1 |

VARIANT_FORMAT_MASTER / 550

| DATA_SET | FORMAT_ID | DATA_TYPE | NUMBER | DESCRIPTION | ETL_LOAD_ID |
|---|---|---|---|---|---|
| e.g. 1 | AD | Integer | , | Allelic depths .. | 1 |
| e.g. 1 | DP | Integer | 1 | Read Depth.. | 1 |
| e.g. 1 | GQ | Float | 1 | Genotype Quality | 1 |
| e.g. 1 | GT | String | 1 | Genotype | 1 |
| e.g. 1 | OG | String | 1 | Orig Genotype input.. | 1 |
| e.g. 1 | PL | Integer | G | Normalized, Phred-scaled.. | 1 |

VARIANT_PLACEHOLDER_MASTER / 560

| DATA_SET | ETL_LOAD_ID |
|---|---|
| e.g. 1 | 1 |
| e.g. 1 | 1 |

FIG. 5

```
CREATE COLUMN TABLE "VARIANT_SOURCE_MASTER" ("DATA_SET" VARCHAR(100),
"ATTRIBUTE_VALUE" VARCHAR(100),
"ATTRIBUTE_NAME" VARCHAR(100),
"ETL_LOAD_ID" INTEGER CS_INT);

CREATE COLUMN TABLE "VARIANT_SAMPLE_MASTER" ("DATA_SET" VARCHAR(100),
"SAMPLE_ID" NVARCHAR(100),
"GENOME" NVARCHAR(512),
"MIXTURE" NVARCHAR(512),
"DESCRIPTION" NVARCHAR(512),
"ETL_LOAD_ID" INTEGER CS_INT);

CREATE COLUMN TABLE "VARIANT_PEDIGREES_MASTER" ("DATA_SET" VARCHAR(100),
"NAME" VARCHAR(100),
"VALUE" VARCHAR(100),
"ETL_LOAD_ID" INTEGER CS_INT);

CREATE COLUMN TABLE "VARIANT_INFO_MASTER" ("DATA_SET" VARCHAR(100),
"DATA_TYPE" VARCHAR(100),
"INFO_ID" VARCHAR(100),
"NUMBER" VARCHAR(100),
"DESCRIPTION" VARCHAR(500),
"ETL_LOAD_ID" INTEGER CS_INT);

CREATE COLUMN TABLE "VARIANT_FORMAT_MASTER" ("DATA_SET" VARCHAR(100),
"DESCRIPTION" VARCHAR(500),
"DATA_TYPE" VARCHAR(100),
"FORMAT_ID" VARCHAR(100),
"NUMBER" VARCHAR(100),
"ETL_LOAD_ID" INTEGER CS_INT);

CREATE COLUMN TABLE "VARIANT_FILTER_MASTER" ("DATA_SET" VARCHAR(100),
"DESCRIPTION" VARCHAR(500),
"FILTER_ID" VARCHAR(100),
"ETL_LOAD_ID" INTEGER CS_INT);

CREATE COLUMN TABLE "VARIANT_CONTIG_MASTER" ("DATA_SET" VARCHAR(100),
"CONTIG_ID" VARCHAR(100),
"NAME" VARCHAR(100),
"VALUE" VARCHAR(100),
"ETL_LOAD_ID" INTEGER CS_INT);

CREATE COLUMN TABLE "VARIANT_ALT_MASTER" ("DESCRIPTION" VARCHAR(100),
"DATA_SET" VARCHAR(100),
"ALT_ID" VARCHAR(100),
"ETL_LOAD_ID" INTEGER CS_INT);
```

| #CHROM | POS | ID | REF | ALT | QUAL | FILTER | INFO | FORMAT | NA00001 | NA00002 | NA00003 |
|---|---|---|---|---|---|---|---|---|---|---|---|
| chr22 | 16053241 | . | C | T | 33 | PASS | AC=3;AF=0.03;AN=94;BaseQ=0.9 | GT:AD:DP:GQ:OG:PL | 0\|0:2,0:2:60:.:0,6,73 | 0\|0:3,0:3:35,23:.:0,9,91 | 0\|0:3,0:3:35,23:.:0,9,82 |
| chr22 | 16053248 | . | T | C | 572 | BGL,Tr99 | AC=12;AF=0.12;AN=94;BaseQ=-2.8 | GT:AD:DP:GQ:OG:PL | 0\|0:2,0:2:60:.:0,3,38 | 0\|0:4,0:4:10,96:.:0,9,92 | 0\|0:4,0:4:10,96:.:0,9,82 |
| chr22 | 16053444 | Rs8016767676 | A | T,GAAATGTA | 469 | PASS | AC=4;AF=0.04;AN=94;BaseQ=-0.9;DB | GT:AD:DP:GQ:OG:PL | 0\|0:4,0:4:30:.:0,12,144 | 0\|0:4,0:4:36,99:.:0,9,108 | 1\|2:4,0:4:40:.:0,12,138 |
| chr22 | 16053791 | Rs117039994 | C | A | 733 | Tr99 | AC=16;AF=0.17;AN=94;BaseQ=-1.3;DB | GT:AD:DP:GQ:OG:PL | 0\|0:4,0:4:60:.:0,9,92 | 0\|2:0,2:7,63:.:0,6,57 | 1\|0:1,1:2:20,92:.:22,0,22 |
| chr22 | 16053814 | Rs113763510 | C | T | 217 | PASS | AC=6;AF=0.064;AN=94;BaseQ=1.0;DB | GT:AD:DP:GQ:OG:PL | 0\|0:3,0:3:28,54:.:0,9,92 | 0\|0:.:.:29,59:./. | 0\|0:3,0:3:40:.:0,9,83 |

430

VARIANT_INFO 810

| DATA_SET | ETL_LOAD_ID | RECORD_COUNT | CHROM | POS | AC_INT_0 | AC_INT_1 | AC_INT_2 ... AC_INT_9 | AF_FLOAT_0 | AF_FLOAT_1 | AF_FLOAT_2 ... AF_FLOAT_9 | AN_INT_0 | BASEQ_FLOAT_0 | DB_VARCHAR1_0 |
|---|---|---|---|---|---|---|---|---|---|---|---|---|---|
| e.g. 1 | 1 | 1 | 22 | 16053241 | null | 3 | null | 0.032 | null | null | 94 | 0.901 | Null |
| e.g. 1 | 1 | 2 | 22 | 16053248 | null | 12 | null | 0.128 | null | null | 94 | -2.808 | Null |
| e.g. 1 | 1 | 3 | 22 | 16053444 | null | 4 | null | 0.043 | null | null | 94 | -0.963 | x |
| e.g. 1 | 1 | 4 | 22 | 16053791 | null | 16 | null | 0.17 | null | null | 94 | -1.317 | x |
| e.g. 1 | 1 | 5 | 22 | 16053814 | null | 6 | null | 0.064 | null | null | 94 | 1.001 | x |

812

VARIANT_SAMPLE 820

| DATA_SET | ETL_LO_AD_ID | RECORD_COUNT | CHROM | POS | GT_INT_0 | GT_INT_1 | GT_PHASED | GT_REST | NONREF_ALLELE_COUNT | AD_INT_0 | AD_INT_1 | AD_INT_2 ... AD_INT_9 | DP_INT_0 | GQ_FLOAT_0 | OG_VARCHAR100_0 | PL_INT_0 | PL_INT_1 | PL_INT_2 | PL_INT_3 ... PL_INT_9 |
|---|---|---|---|---|---|---|---|---|---|---|---|---|---|---|---|---|---|---|---|
| e.g. 1 | 1 | 1 | 22 | 16053241 | 0 | 0 | \| | null | 0 | 2 | 0 | null | 2 | 60 | null | 0 | 0 | 6 | 73 |
| e.g. 1 | 1 | 1 | 22 | 16053241 | 0 | 0 | \| | null | 0 | 3 | 0 | null | 3 | 22.29 | null | 0 | 0 | 9 | 91 |
| e.g. 1 | 1 | 1 | 22 | 16053241 | 0 | 0 | \| | null | 0 | 3 | 0 | null | 3 | 35.23 | null | 0 | 0 | 9 | 82 |
| e.g. 1 | 1 | 2 | 22 | 16053248 | 0 | 0 | \| | null | 0 | 2 | 0 | null | 2 | 60 | null | 0 | 0 | 3 | 38 |
| e.g. 1 | 1 | 2 | 22 | 16053248 | 0 | 0 | \| | null | 0 | 4 | 0 | null | 4 | 10.96 | null | 0 | 0 | 9 | 92 |
| e.g. 1 | 1 | 3 | 22 | 16053444 | 0 | 0 | \| | null | 0 | 4 | 0 | null | 4 | 10.96 | null | 0 | 0 | 9 | 82 |
| e.g. 1 | 1 | 3 | 22 | 16053444 | 1 | 0 | \| | null | 2 | 4 | 0 | null | 4 | 30 | null | 0 | 0 | 12 | 144 |
| e.g. 1 | 1 | 4 | 22 | 16053791 | 0 | 0 | \| | null | 0 | 4 | 0 | null | 4 | 36.99 | null | 0 | 0 | 9 | 108 |
| e.g. 1 | 1 | 4 | 22 | 16053791 | 1 | 0 | \| | null | 1 | 2 | 1 | null | 2 | 40 | null | 0 | 0 | 12 | 138 |
| e.g. 1 | 1 | 4 | 22 | 16053791 | 0 | 0 | \| | null | 1 | 1 | 1 | null | 2 | 60 | null | 0 | 0 | 6 | 92 |
| e.g. 1 | 1 | 5 | 22 | 16053814 | 1 | 0 | \| | null | 0 | 2 | 0 | null | 2 | 7.63 | null | 22 | 0 | 9 | 67 |
| e.g. 1 | 1 | 5 | 22 | 16053814 | 0 | 0 | \| | null | 1 | 3 | 0 | null | 2 | 20.92 | null | 0 | 22 | 0 | 22 |
| e.g. 1 | 1 | 5 | 22 | 16053814 | 0 | 0 | \| | null | 0 | null | null | null | 3 | 28.54 | null | null | null | null | 92 |
| e.g. 1 | 1 | 5 | 22 | 16053814 | 0 | 0 | \| | null | 0 | 3 | 0 | null | 3 | 29.59 | null | 0 | null | 9 | null |
| e.g. 1 | 1 | 5 | 22 | 16053814 | 0 | 0 | \| | null | 0 | 3 | 0 | null | 3 | 40 | null | 0 | 0 | 9 | 83 |

```
CREATE COLUMN TABLE "VARIANT_ALTERNATE" ("DATA_SET" VARCHAR(100),
    "RECORD_COUNT" INTEGER CS_INT,
    "INDEX" INTEGER CS_INT,
    "ALLELE" TEXT,
    "ALLELE_LENGTH" BIGINT CS_FIXED,
    "ETL_LOAD_ID" INTEGER CS_INT,
    "CHROM" VARCHAR(100),
    "POS" INTEGER CS_INT);

CREATE COLUMN TABLE "VARIANT_ANNOTATION" ("DATA_SET" VARCHAR(100),
    "RS_ID" VARCHAR(100),
    "CHROM" VARCHAR(100),
    "POS" BIGINT CS_FIXED,
    "SOURCE_TYPE" VARCHAR(100),
    "NOTES" VARCHAR(500),
    "ETL_LOAD_ID" INTEGER CS_INT,
    "RECORD_COUNT" INTEGER CS_INT);

CREATE COLUMN TABLE "VARIANT_FILTER" ("DATA_SET" VARCHAR(100),
    "RECORD_COUNT" INTEGER CS_INT,
    "FILTER_ID" VARCHAR(100),
    "ETL_LOAD_ID" INTEGER CS_INT,
    "CHROM" VARCHAR(100),
    "POS" INTEGER CS_INT);

CREATE COLUMN TABLE "VARIANT_MASTER" ("DATA_SET" VARCHAR(100),
    "RECORD_COUNT" INTEGER CS_INT,
    "CHROM" VARCHAR(100),
    "POS" BIGINT CS_FIXED,
    "QUAL" INTEGER CS_INT,
    "ETL_LOAD_ID" INTEGER CS_INT);

CREATE COLUMN TABLE "VARIANT_INFO" ("DATA_SET" VARCHAR(100),
    "RECORD_COUNT" INTEGER CS_INT,
    "ETL_LOAD_ID" VARCHAR(100),
    "CHROM" VARCHAR(100),
    "POS" INTEGER CS_INT
    (<viewable attributes>));

CREATE COLUMN TABLE "VARIANT_SAMPLE" ("DATA_SET" VARCHAR(100),
    "SAMPLE_ID" VARCHAR(100),
    "RECORD_COUNT" INTEGER CS_INT,
    "ETL_LOAD_ID" INTEGER CS_INT,
    "CHROM" VARCHAR(100),
    "POS" BIGINT CS_FIXED,
    "GT_INT_0" INTEGER CS_INT,
    "GT_PHASED" VARCHAR(1),
    "GT_INT_1" INTEGER CS_INT,
    "GT_REF" VARCHAR(100),
    "NONREF_ALLELE_COUNT" INTEGER CS_INT
    (<viewable attributes>));
```

| VARIANT_LOOKUP | | | | | | |
|---|---|---|---|---|---|---|
| DATA SET | ETL_LOAD_ID | TYPE | VCF_FIELD_NAME | INDEX | TABLE_NAME | COLUMN_NAME |
| e.g. 1 | 1 | FORMAT | AD | 0 | VARIANT_SAMPLE | AD_INT_0 |
| e.g. 1 | 1 | FORMAT | AD | 1 | VARIANT_SAMPLE | AD_INT_1 |
| e.g. 1 | 1 | FORMAT | DP | 0 | VARIANT_SAMPLE | DP_INT_0 |
| e.g. 1 | 1 | FORMAT | GQ | 0 | VARIANT_SAMPLE | GQ_FLOAT_0 |
| e.g. 1 | 1 | FORMAT | OG | 0 | VARIANT_SAMPLE | OG_VARCHAR100_0 |
| e.g. 1 | 1 | FORMAT | PL | 0 | VARIANT_SAMPLE | PL_INT_0 |
| e.g. 1 | 1 | FORMAT | PL | 1 | VARIANT_SAMPLE | PL_INT_1 |
| e.g. 1 | 1 | FORMAT | PL | 2 | VARIANT_SAMPLE | PL_INT_2 |
| e.g. 1 | 1 | INFO | AC | 1 | VARIANT_INFO | AC_INT_1 |
| e.g. 1 | 1 | INFO | AF | 1 | VARIANT_INFO | AF_FLOAT_1 |
| e.g. 1 | 1 | INFO | AN | 0 | VARIANT_INFO | AN_INT_0 |
| e.g. 1 | 1 | INFO | BASEQ | 0 | VARIANT_INFO | BASEQ_FLOAT_0 |
| e.g. 1 | 1 | INFO | DB | 0 | VARIANT_INFO | DB_VARCHAR1_0 |

```
CREATE COLUMN TABLE "GENOMINDEV"."VARIANT_LOOKUP" ("DATA_SET" VARCHAR(100),
"TYPE" VARCHAR(100),
"VCF_FIELD_NAME" VARCHAR(100),
"INDEX" INTEGER CS_INT,
"TABLE_NAME" VARCHAR(100),
"COLUMN_NAME" VARCHAR(100),
"ETL_LOAD_ID" INTEGER CS_INT);
```
— 1110

```
Parse info field of VCF
split up key/value pairs at the symbol ";"
for each key/value pair:
    Split up key/value pair into INFO_ID = key and set of values
    Lookup DATA_TYPE and NUMBER in VARIANT_INFO_MASTER for INFO_ID
    Split up set of values at "," (use NUMBER as an indicator for max INDEX)
    If column(s) with name <INFO_ID>_<DATA_TYPE>_INDEX_do(es) not exist in
    VARIANT_LOOKUP for this DATA_SET/ETL_LOAD_ID combination:
        Alter table VARIANT_INFO add column(s) <INFO_ID>_<DATA_TYPE>_INDEX
        Update VARIANT_LOOKUP table with according information
    Insert data into VARIANT_INFO table
```
— 1120

MAPPING OF EXTENSIBLE DATASETS TO RELATIONAL DATABASE SCHEMAS

CROSS-REFERENCE TO RELATED APPLICATION

This application claims priority to U.S. Patent Application Ser. No. 61/940,198 filed on Feb. 14, 2014, entitled "Mapping of Extensible Datasets to Relational Database Schemas," the contents of which are incorporated by reference herewith in its entirety.

TECHNICAL FIELD

The subject matter described herein relates to the mapping of complex and evolving datasets that offer extensibility, such as datasets arranged according to the variant call format (VCF), to a relational database schema, as well as to related data structures.

BACKGROUND

Variant call format is a standardized, yet evolving, format of a text file used in bioinformatics for storing gene sequence variations. Instead of storing all genetic data, which can result in significant duplications and/or overlap, only variations are stored along with a corresponding reference genome. Analysis of such text files, while simpler than analyzing all genetic data according to a general feature format (GFF), can be lengthy and additionally consume significant process resources.

SUMMARY

In one aspect, data including a text file is received. The text file is arranged in an extensible format and includes a plurality of metadata lines, a header line, and a plurality of content lines. Metadata from the metadata lines is mapped to a plurality of metadata tables in a database that are formed according to a relational database schema using prefix parameters from each metadata line. Content from the content lines is mapped to a plurality of content tables in the database that are formed according to the relational database schema using the header line. A first subset of the content tables have a static structure and a second subset of the content tables have a dynamic structure. The mapping of content from the content lines to a plurality of content tables includes mapping gene sequence variations to corresponding reference genome position where the gene sequence variations occur. The text file is arranged according to the genomic variant call format. Generating the metadata tables includes using the prefix parameters to determine at least one of a metadata table name, number of columns and data types for the columns. Key-value pairs are identified from each metadata line. Contents from metadata lines that contain only one key-value pair are stored in single key-value pair metadata tables, which include a single column for the keys from all the metadata lines and a corresponding column for values from all the metadata lines. Contents from metadata lines that contain multiple key-value pairs are stored in multiple key-value pair metadata tables comprising a column for each unique key. The column is named after the key, and the corresponding values are mapped into the rows of the columns named after the keys.

Mapping content from the content lines to a plurality of content tables can include identifying header parameters from the header line, and generating content tables with the header parameters from the header line defining the content tables names within the relational database. Each content table can include at least a column storing contents associated with the header parameter defining the name of the content table.

If it is determined that the header parameter has more than one corresponding value, an additional row in the content table can be generated under the header parameter for each corresponding value, and a record count can be incremented by one with each additional row. The header parameters from the header line can include at least one of a position, identification, alternate, quality and filter parameter. An alternates content table can store reference alleles and corresponding alternate alleles. The alternates content table can include at least one column storing both the reference allele and corresponding alternate allele at a particular chromosome position. Each reference allele and corresponding alternate alleles at a particular chromosome position can be mapped into separate rows in the column. A record count value can increment by one with each additional row, and an index number, starting at zero to represent the reference allele, can increment by one for each alternate allele mapped into each additional row. The alternate content table can include an allele length column.

The database can include a columnar data store storing database tables as sections of columns. The database can be an in-memory database storing the metadata tables and the content tables in main memory.

Non-transitory computer program products (i.e., physically embodied computer program products) are also described that store instructions, which when executed on one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the current subject matter enables the relational representation of complex and evolving data schemas such as the variant call format which, in turn, enables more rapid analysis of underlying data while consuming fewer processing (CPU, memory, I/O, etc.) resources.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 4 is an example of a variant call format (VCF) file consistent with one or more features of the current subject matter.

FIG. 5 is a diagram illustrating an example of metadata mapping from a VCF file format into tables within a relational database.

FIG. 6 is a diagram illustrating an example of source code that can be used to create the metadata tables for mapping the metadata of a VCF file into.

FIG. 8 is a diagram illustrating an example of content mapping from a VCF file format into dynamic tables within a relational database.

FIG. 9 is a diagram illustrating an example of source code that can be used to create the content data tables for mapping the content lines of a VCF file into.

FIG. 10 is a diagram illustrating an example of a lookup table that matches the dynamically created columns to the original keys from the VCF file.

FIG. 11 is a diagram illustrating an example of source code and a pseudo-code algorithm that can be used to create and match the columns of lookup tables as described.

Like reference symbols in the various drawings indicate like elements.

DETAILED DESCRIPTION

Figure 1:
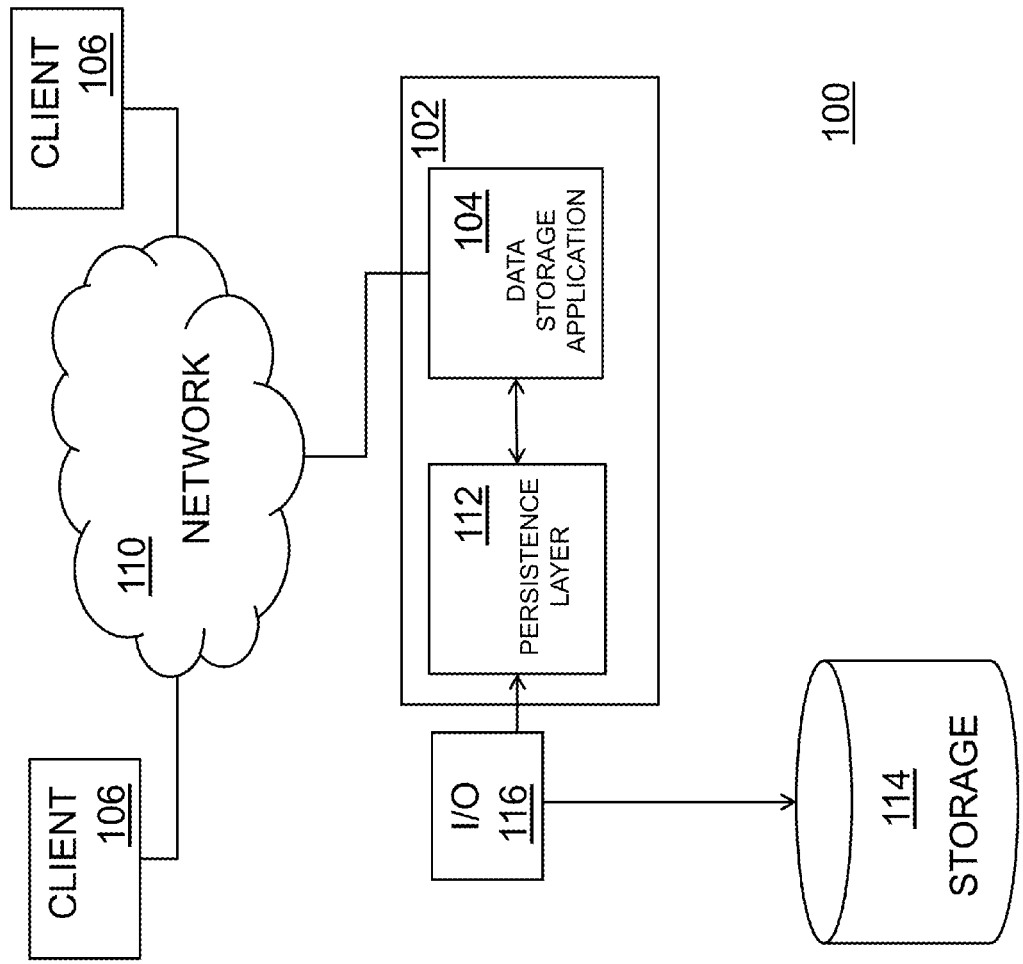
FIG. 1 is a diagram illustrating a system including a data storage application.
Figure 2:
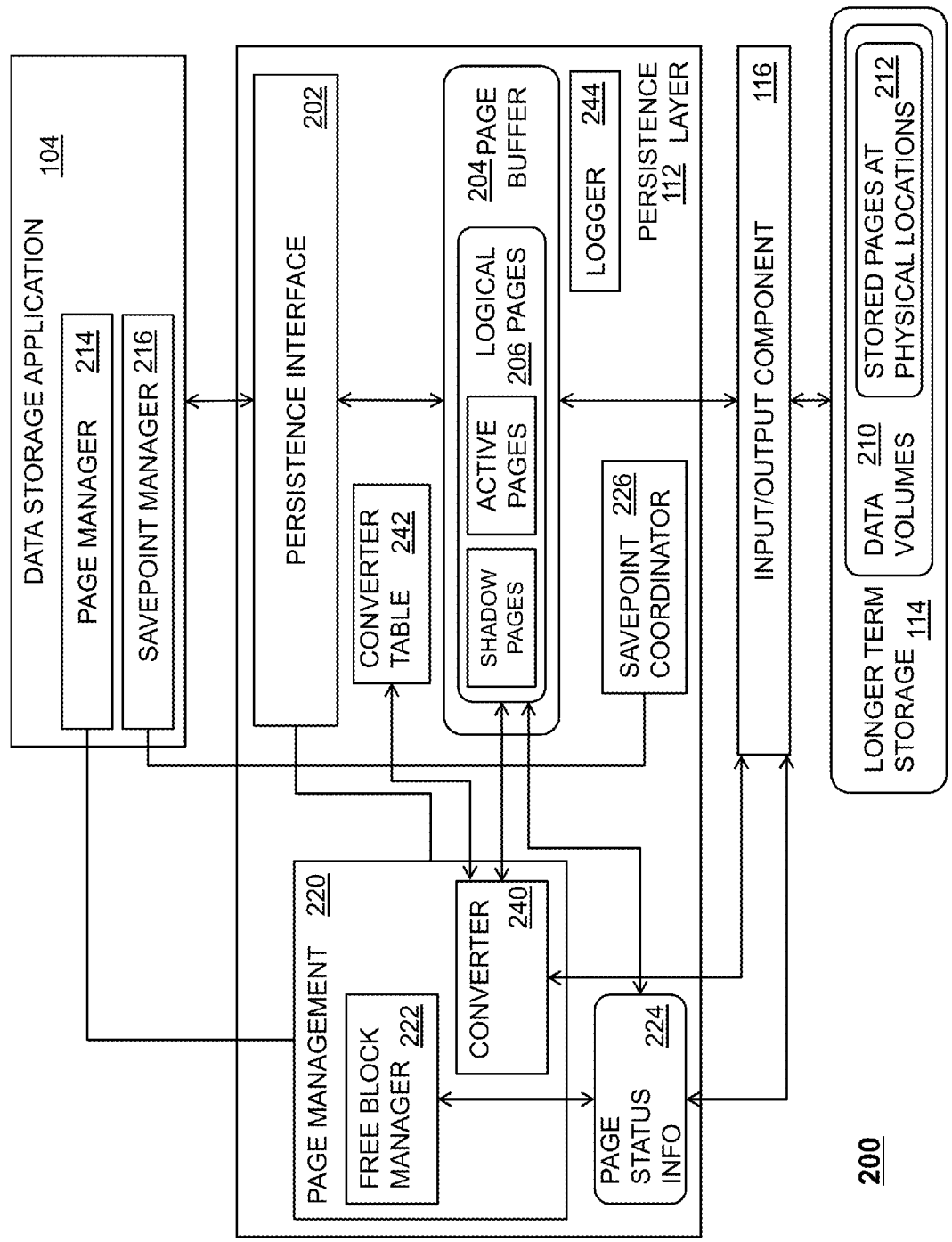
FIG. 2 is a diagram illustrating details of the system of FIG. 1.
Figure 3:
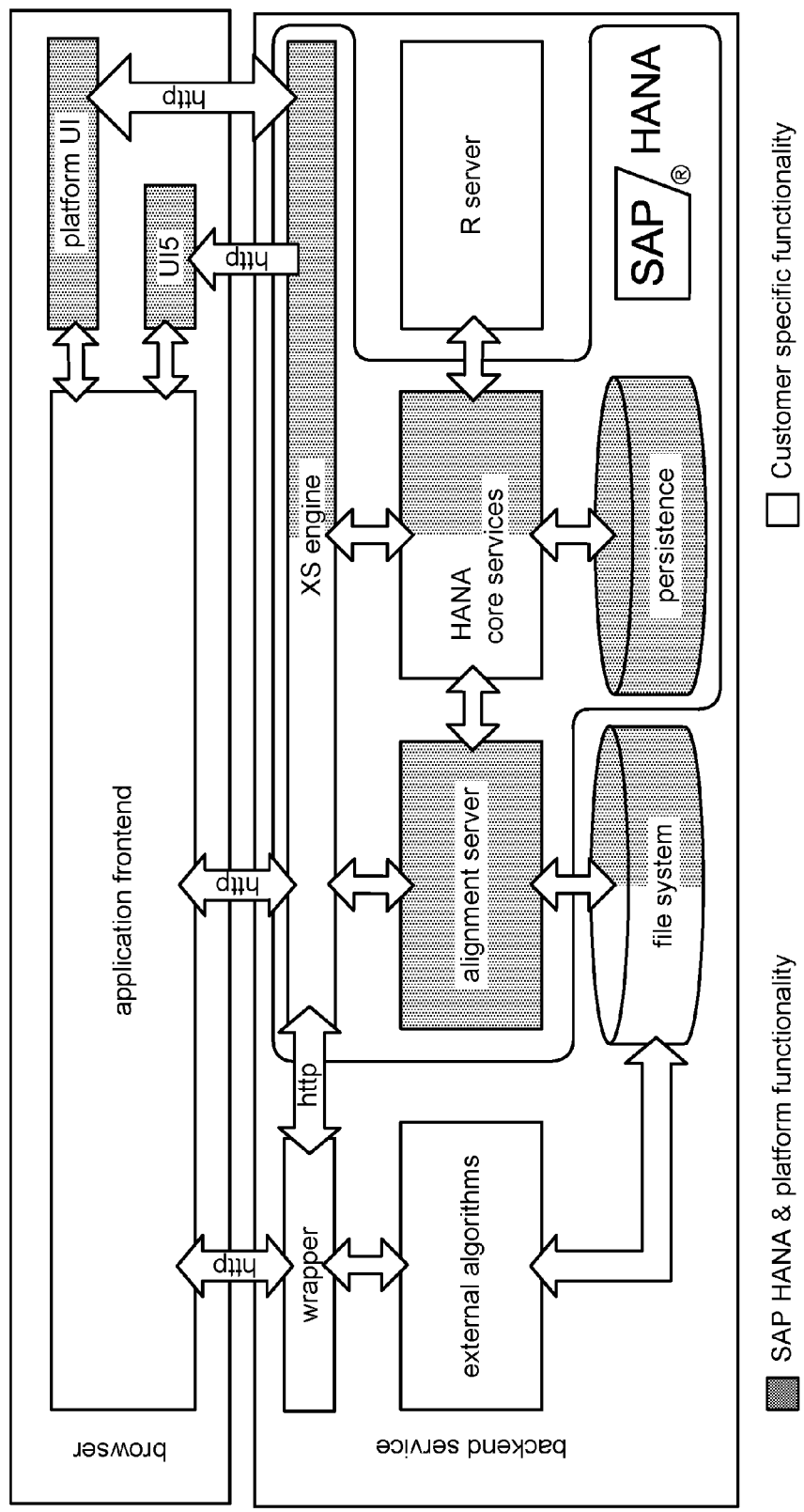
FIG. 3 is a diagram illustrating integration of the system of FIGS. 1 and 2 into a particular customer system.

FIGS. 1-3 are diagrams providing an example environment for implementing the subject matter described herein. It will be appreciated that other environments can be utilized including variations of the environments illustrated in FIGS. 1-3. FIGS. 1 and 2 illustrate a generic computing environment and FIG. 3 is a diagram 300 illustrating a particular implementation using the SAP HANA platform. In particular, FIG. 1 shows an example of a system 100 in which a computing system 102, which can include one or more programmable processors that can be collocated, linked over one or more networks, etc., executes one or more modules, software components, or the like of a data storage application 104. The data storage application 104 can include one or more of a database, an enterprise resource program, a distributed storage system (e.g. NetApp Filer available from NetApp of Sunnyvale, Calif.), or the like.

The one or more modules, software components, or the like can be accessible to local users of the computing system 102 as well as to remote users accessing the computing system 102 from one or more client machines 106 over a network connection 110. One or more user interface screens produced by the one or more first modules can be displayed to a user, either via a local display or via a display associated with one of the client machines 106. Data units of the data storage application 104 can be transiently stored in a persistence layer 112 (e.g. a page buffer or other type of temporary persistency layer), which can write the data, in the form of storage pages, to one or more storages 114, for example via an input/output component 116. The one or more storages 114 can include one or more physical storage media or devices (e.g. hard disk drives, persistent flash memory, random access memory, optical media, magnetic media, and the like) configured for writing data for longer term storage. It should be noted that the storage 114 and the input/output component 116 can be included in the computing system 102 despite their being shown as external to the computing system 102 in FIG. 1.

Data retained at the longer term storage 114 can be organized in pages, each of which has allocated to it a defined amount of storage space. In some implementations, the amount of storage space allocated to each page can be constant and fixed. However, other implementations in which the amount of storage space allocated to each page can vary are also within the scope of the current subject matter.

FIG. 2 shows a software architecture 200 consistent with one or more features of the current subject matter. A data storage application 104, which can be implemented in one or more of hardware and software, can include one or more of a database application, a network-attached storage system, or the like. According to at least some implementations of the current subject matter, such a data storage application 104 can include or otherwise interface with a persistence layer 112 or other type of memory buffer, for example via a persistence interface 202. A page buffer 204 within the persistence layer 112 can store one or more logical pages 206, and optionally can include shadow pages, active pages, and the like. The logical pages 206 retained in the persistence layer 112 can be written to a storage (e.g. a longer term storage, etc.) 114 via an input/output component 116, which can be a software module, a sub-system implemented in one or more of software and hardware, or the like. The storage 114 can include one or more data volumes 210 where stored pages 212 are allocated at physical memory blocks.

In some implementations, the data storage application 104 can include or be otherwise in communication with a page manager 214 and/or a savepoint manager 216. The page manager 214 can communicate with a page management module 220 at the persistence layer 112 that can include a free block manager 222 that monitors page status information 224, for example the status of physical pages within the storage 114 and logical pages in the persistence layer 112 (and optionally in the page buffer 204). The savepoint manager 216 can communicate with a savepoint coordinator 226 at the persistence layer 204 to handle savepoints, which are used to create a consistent persistent state of the database for restart after a possible crash.

In some implementations of a data storage application 104, the page management module of the persistence layer 112 can implement a shadow paging. The free block manager 222 within the page management module 220 can maintain the status of physical pages. The page buffer 204 can included a fixed page status buffer that operates as discussed herein. A converter component 240, which can be part of or in communication with the page management module 220, can be responsible for mapping between logical and physical pages written to the storage 114. The converter 240 can maintain the current mapping of logical pages to the corresponding physical pages in a converter table 242. The converter 240 can maintain a current mapping of logical pages 206 to the corresponding physical pages in one or more converter tables 242. When a logical page 206 is read from storage 114, the storage page to be loaded can be looked up from the one or more converter tables 242 using the converter 240. When a logical page is written to storage 114 the first time after a savepoint, a new free physical page is assigned to the logical page. The free block manager 222 marks the new physical page as "used" and the new mapping is stored in the one or more converter tables 242.

The persistence layer 112 can ensure that changes made in the data storage application 104 are durable and that the data storage application 104 can be restored to a most recent committed state after a restart. Writing data to the storage 114 need not be synchronized with the end of the writing transaction. As such, uncommitted changes can be written to disk and committed changes may not yet be written to disk when a writing transaction is finished. After a system crash, changes made by transactions that were not finished can be rolled back. Changes occurring by already committed transactions should not be lost in this process. A logger component 344 can also be included to store the changes made to the data of the data storage application in a linear log. The logger component 244 can be used during recovery to replay operations since a last savepoint to ensure that all operations are applied to the data and that transactions with a logged "commit" record are committed before rolling back still-open transactions at the end of a recovery process.

With some data storage applications, writing data to a disk is not necessarily synchronized with the end of the writing transaction. Situations can occur in which uncommitted changes are written to disk and while, at the same time, committed changes are not yet written to disk when the writing transaction is finished. After a system crash, changes made by transactions that were not finished must be rolled back and changes by committed transaction must not be lost.

To ensure that committed changes are not lost, redo log information can be written by the logger component 244 whenever a change is made. This information can be written to disk at latest when the transaction ends. The log entries can be persisted in separate log volumes while normal data is written to data volumes. With a redo log, committed changes can be restored even if the corresponding data pages were not written to disk. For undoing uncommitted changes, the persistence layer 112 can use a combination of undo log entries (from one or more logs) and shadow paging.

The persistence interface 202 can handle read and write requests of stores (e.g., in-memory stores, etc.). The persistence interface 202 can also provide write methods for writing data both with logging and without logging. If the logged write operations are used, the persistence interface 202 invokes the logger 244. In addition, the logger 244 provides an interface that allows stores (e.g., in-memory stores, etc.) to directly add log entries into a log queue. The logger interface also provides methods to request that log entries in the in-memory log queue can be flushed to disk.

Log entries contain a log sequence number, the type of the log entry and the identifier of the transaction. Depending on the operation type additional information is logged by the logger 244. For an entry of type "update," for example, this would be the identification of the affected record and the after image of the modified data.

When the data application 104 is restarted, the log entries need to be processed. To speed up this process the redo log is not always processed from the beginning. Instead, as stated above, savepoints can be periodically performed that write all changes to disk that were made (e.g., in memory, etc.) since the last savepoint. When starting up the system, only the logs created after the last savepoint need to be processed. After the next backup operation the old log entries before the savepoint position can be removed.

When the logger 244 is invoked for writing log entries, it does not immediately write to disk. Instead it can put the log entries into a log queue in memory. The entries in the log queue can be written to disk at the latest when the corresponding transaction is finished (committed or aborted). To guarantee that the committed changes are not lost, the commit operation is not successfully finished before the corresponding log entries are flushed to disk. Writing log queue entries to disk can also be triggered by other events, for example when log queue pages are full or when a savepoint is performed.

With the current subject matter, the logger 244 can write a database log (or simply referred to herein as a "log") sequentially into a memory buffer in natural order (e.g., sequential order, etc.). If several physical hard disks/storage devices are used to store log data, several log partitions can be defined. Thereafter, the logger 244 (which as stated above acts to generate and organize log data) can load-balance writing to log buffers over all available log partitions. In some cases, the load-balancing is according to a round-robin distributions scheme in which various writing operations are directed to log buffers in a sequential and continuous manner. With this arrangement, log buffers written to a single log segment of a particular partition of a multi-partition log are not consecutive. However, the log buffers can be reordered from log segments of all partitions during recovery to the proper order.

As stated above, the data storage application 104 can use shadow paging so that the savepoint manager 216 can write a transactionally-consistent savepoint. With such an arrangement, a data backup comprises a copy of all data pages contained in a particular savepoint, which was done as the first step of the data backup process. The current subject matter can be also applied to other types of data page storage.

The data storage application 104 can utilize multi-version concurrent control (MVCC) for transaction isolation and consistent reading. Each row of the database can be associated with a unique, monotonically-increasing identifier (RowID). When a new version of the record is created, this new version can also become a new RowID (i.e., due to MVCC semantics, old versions must be kept for parallel readers and will be cleaned only during garbage collection after commit).

References herein to pages can refer to pages of a table stored in memory of an in-memory database forming part of the data storage application 104. With the MVCC-based database table implementation, all internal transient data objects of a table can be versioned. These data objects can include table a header object, metadata object(s), other internal state(s) such as vector of loaded pages, dictionary hashes/trees for compressed columnar tables, and the like. In addition, all table control structures used by readers can be versioned. These structures include, for example, page lists, value indirection vectors, internal metadata, and more. Readers do not acquire any locks on data structure, but rather, work with a current version of a data structure until query or query plan operator ends. With this arrangement, old versions only remain for a short period of time (e.g., sub-seconds). As versioned objects are typically small, memory overhead is also small. In addition, even with OLTP systems, incompatible changes are rare (i.e., there are not many concurrent versions, etc.). Moreover, with some implementations, if older versions of prioritized/big objects (e.g., main part of a columnar table, etc.) still exist, no new version of the corresponding object can be created. For example, if there is a reader doing a scan on the main part of a columnar table, which started during columnar table merge from version n−1 to version n, this scan uses main part in version n−1. Even after merge to version n is finished, further merge from version n to version n+1 will be prevented as long as there are any scans running on main part in version n−1 (as this might increase memory demand prohibitively).

As noted, above the current subject matter is directed to mapping data that has an extensible format, such as the variant call format, to a relational database schema for use by the data storage application 104. While the foregoing is described predominantly with regard variant call format, it will be appreciated that the current subject matter is also applicable to other data formats having similar features and attributes.

FIG. 4 shows an example for the contents of a variant call format (VCF) file 400 consistent with one or more features of the current subject matter. Variant call format is a standardized format of a text file used in bioinformatics for storing genetic variant data, or variations in genetic data. Instead of storing all genetic data, which can result in significant duplications and/or overlap, only variations can be stored along with a corresponding reference genome. Analysis of such text files, while simpler than analyzing all genetic data according to a general feature format (GFF), can be lengthy and additionally consume significant process resources.

VCF is a continually evolving standard that can be likely subject to change in the future. The example in FIG. 4 shows mapping according to version VCF 4.2. VCF can provide variant location by source, chromosome, and position, and the details can differ for both position and source. The file can contain metadata lines 410, a header line 420, and content lines 430. The metadata lines 410 can begin with "##" and they may contain information that can be used to interpret the contents lines 430 in the VCF file 400. The header line 420 can begin with "#CHROM" and can provide the column structure for the data in the content lines 430. The metadata lines 410 can be varied, and only a limited subset of the information in the metadata lines 410 may need to be fixed to a predefined structure. Most of the information in these metadata lines 410 is optional and the creator of a VCF file 400 can specify the contents of these lines freely only following the given VCF format.

The VCF file may not be provided in a relational database friendly format. In order to convert the information into a relational database format, detailed mapping strategies are required. The VCF file can include diverse data types, fields presented in a non-standard form, as well as specific symbols (for example "##", and "|"), which have specific non-standard database nomenclature—all of which may need to be mapped in order to convert the information from the VCF file into a relational database format. Additionally, VCF format allows a file creator to dynamically and flexibly change (add or remove) data types as well as the amount of data residing in these different data types. Due to the fact that VCF is an "open" format, i.e. users can specify their own fields to store additional data, the mapping needs to accommodate flexibility. Using a robust relational database can improve the efficiency and speed of running queries on the information in VCF files, therefore the mapping of the VCF format to a relational database can lead to significant benefits to science. The mapping described in the following can rely on the ability of a column-oriented database to dynamically add new columns to an existing table, during runtime. Thus, the relational database schema can evolve over time (i.e., the schema is extensible).

FIG. 5 is a diagram illustrating an example of metadata mapping from a VCF file format into tables within a relational database. The metadata lines 410 of VCF file 400, from FIG. 4 can be mapped into five metadata tables shown as 510-550. It is understood that the metadata lines 410 can be mapped onto a larger number (or smaller number) of tables depending on the information provided in these metadata lines 410, as well as based on the mapping strategy defined. General columns that can occur in all tables are the "DATA_SET" and "ETL_LOAD_ID" columns. These can ensure the link between imported data and the original VCF files. Metadata tables 510, 530 and 540 can use a key/value store format strategy instead of the traditional relational model of mapping data to named columns. The rationale behind this is that metadata, as mentioned above, can be specified by VCF file creators and thus may vary greatly over a set of files. The amount of metadata provided, however, may be very limited per file. Thus, using the key/value approach appears to be the best approach, as these tables will grow slowly using the key/value approach. Furthermore, it can be assumed that the metadata in the tables are rarely used at query time, and even if it is being used, it is not necessary to reconstruct the former lines, as they are present in the original VCF file. Such a reconstruction would entail self-joins of tables that would quickly become expensive with growing table sizes.

The table VARIANT SOURCE MASTER 510 is a table mapping source type parameter and has a simple key/value pair format that maps all metadata lines with simple key value pairs of a format similar to "##fileformat=VCFv4.2," for example, the lines 1-4, and 6 of metadata content 410.

The table VARIANT INFO MASTER 520 is a table mapping information type parameters provided by the lines starting with "##INFO", e.g. lines 7-12. filling the columns according to the keys and values given in the section between the symbols "<", ">". Another table following a similar approach is the VARIANT FORMAT MASTER 550 table mapping format parameters contained in the lines starting with "##FORMAT", e.g. lines 15-20 of metadata content 410. Similarly VARIANT_FILTER_MASTER table 540 maps filter parameters found in the lines starting with "##FILTER", e.g. lines 13 and 14 of metadata content 410. Additional tables, for example "VARIANT ALT MASTER", and "VARIANT SAMPLE MASTER" (not shown in FIG. 5) map metadata lines 410 starting with "##ALT" and "##SAMPLE", accordingly, and can follow the same approach as used in the VARIANT INFO MASTER 520 table.

Lines from metadata content 410 that have a similar format as line 5 are mapped to the table VARIANT CONTIG MASTER table 530. This table does not have columns for all the possible keys that might occur like the VARIANT INFO MASTER table 520. Instead, all key/value pairs except "ID," are stored in the key/value format. "ID" is stored in the "CONTIG_ID" column. The mapping to the VARIANT PEDIGREES MASTER table (not shown) follows the same approach with all lines starting with "##PEDIGREE". It is naturally understood that following a similar logic, other metadata tables entitled "VARIANT PLACEHOLDER MASTER" can be created to map parameters of type PLACEHOLDER, and whose metadata lines may begin with "##PLACEHOLDER", where this "PLACEHOLDER" may be any type of parameter.

FIG. 6 is a diagram illustrating an example of source code that can be used to create the metadata tables for mapping the metadata of a VCF file into. Source code 600 provides examples of the columns, as well as data types e.g. varchar of size 100, or integer, that can be defined in each of the metadata tables described above.

Figure 7:
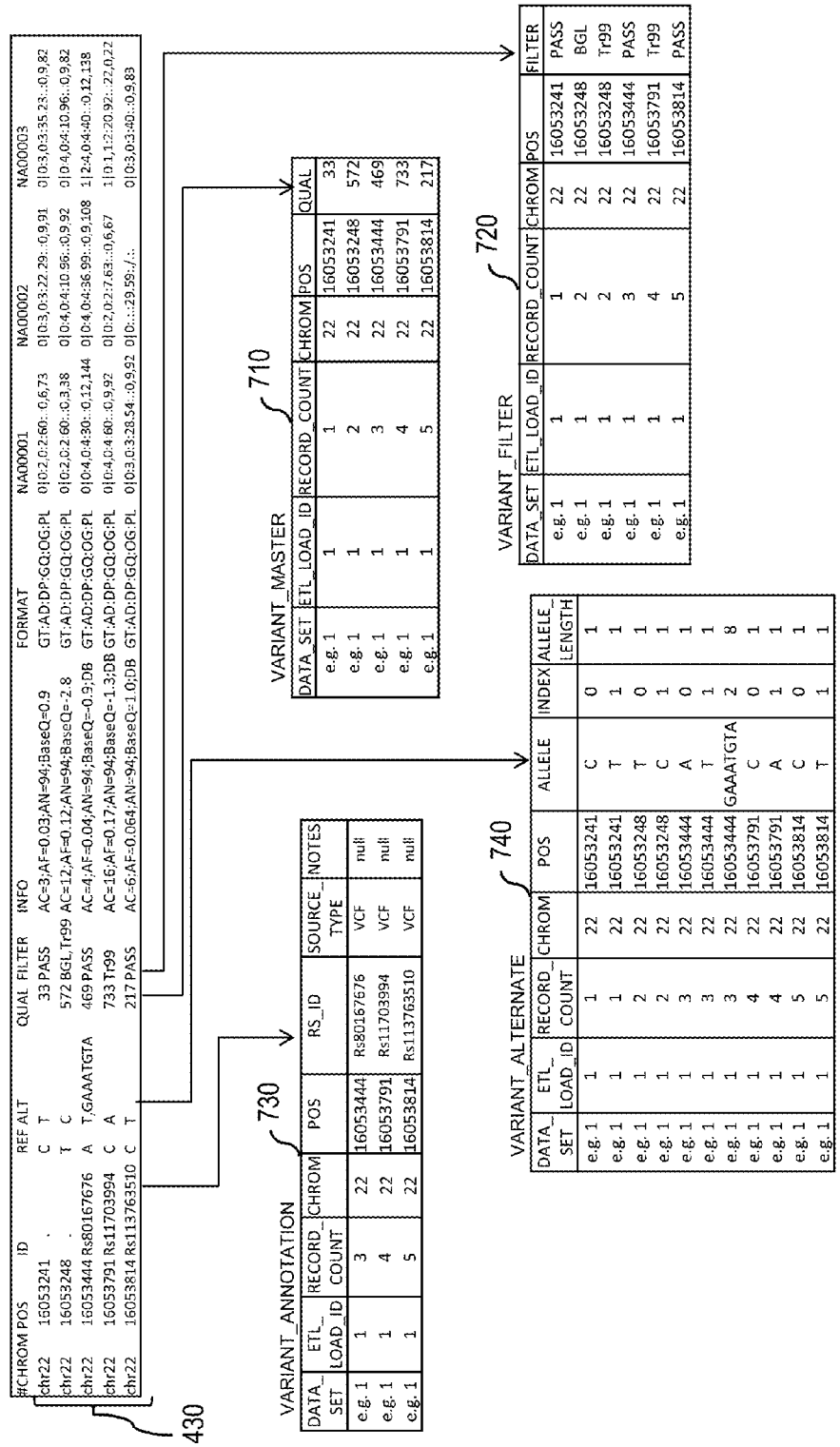
FIG. 7 is a diagram illustrating an example of content mapping from a VCF file format into static tables within a relational database.

FIGS. 7 and 8 are diagrams illustrating an example of content mapping from a VCF file format into tables within a relational database. The content lines 430 of VCF file 400, from FIG. 4 can be mapped into content tables shown as 710-740, 810, and 820. It is understood that the content lines 430 can be mapped onto a larger number (or smaller number) of tables depending on the information provided in these content lines 430, as well as based on the mapping strategy defined. General columns that can occur in all tables are the "DATA_SET" and "ETL_LOAD_ID" columns. These can ensure the link between imported data and the original VCF files. In addition to the "DATA SET" and "ETL LOAD ID" columns, all these tables can store the chromosome "CHROM" and position "POS" where a specific variant has been encountered.

The VARIANT MASTER table 710 includes a quality column entitled "QUAL," into which the quality values from the content lines 430 are mapped. The VARIANT FILTER table 720 includes a filter column entitled "FILTER," and can record the filters that have passed or failed. Each line in the contents line section 430 may have several filters assigned to it. Therefore, in order to normalize the data, filter data can be stored in its own table. The VARIANT ANNOTATION table 730 can include an Rs identifier column entitled "RS_ID." Similar to the filters described above, each content line may have zero or more annotations associated with it. These annotation values can be stored in the VARIANT ANNOTATION table 730. The VARIANT ALTERNATE table 740 is the largest of these six tables, because for each line this table stores several rows. One row can be required for each allele specified in the "REF" and "ALT" fields of a VCF file. The "INDEX" column can be used to interpret which allele is stored. The value "0" always stands for the reference allele, that is the allele that the reference genome shows at this position in the chromosome. Accordingly, the index is incremented for each alternate allele specified in the "ALT" field. The genotype information given for each sample uses the "INDEX" column to reference the allele values. Storing indices instead of the actual values for the allele spurts the advantage that researches can easily determine the share of variation in a cohort as "0" stands for the reference genome and any other value stands for a variation. The actual value of the allele can be stored in the "ALLELE" column. The values stored here can be any strings of arbitrary length composed of the alphabet "A," "C," "G," and "T."

The VARIANT MASTER 710, VARIANT FILTER 720, VARIANT ANNOTATION 730, and VARIANT ALTERNATE 740 tables can be of a static structure. The VARIANT INFO 810 and VARIANT SAMPLE 820 tables can be of a dynamic structure, and these tables can evolve over time such that columns can be added during the runtime of the system. The group of dynamic columns 812 and 822 are examples of this dynamic structure of the VARIANT INFO table 810 and the VARIANT SAMPLE table 820, respectively.

The VARIANT INFO table 810 can record all the key/value pairs specified in the "INFO" field of a content line. Instead of storing key/value pairs the chosen approach can utilize the benefit of a column-oriented database to easily add columns during the runtime of the system, therefore the table can grow during the lifetime of the application. This approach can require an additional structure, for example a lookup table, described in FIG. 10, to match the dynamically created columns to the original keys from the VCF file.

FIG. 9 is a diagram illustrating an example of source code that can be used to create the content data tables for mapping the content lines of a VCF file into. Source code 900 provides examples of the columns, as well as data types e.g. varchar of size 100, or integer, that can be defined in each of the content tables described above.

FIG. 10 is a diagram illustrating an example of a lookup table that matches the dynamically created columns to the original keys from the VCF file. Lookup table 1010 can store the names of the original fields in the VCF and their mapping to new created columns in the dynamic VARIANT INFO 810, or VARIANT SAMPLE 820 tables. For example, the first line of VARIANT_LOOKUP table 1010 maps the field name "AD" found in the content section 430 and INDEX value "0" map onto the dynamically generated column "AD_INT_0" that can be found in the VARIANT SAMPLE table 820. The remainder of the lines of VARIANT_LOOKUP table 1010 follow a similar mapping, by the dynamic columns 812 and 822 to the original keys in the VCF file 400.

FIG. 11 is a diagram illustrating an example of source code and a pseudo-code algorithm that can be used to create and match the columns of lookup tables as described. Source code 1110 provides examples of the columns, as well as data types e.g. varchar of size 100, or integer, that can be defined for the columns of lookup table 1010. Pseudo-code 1120 can provide a process for column matching and creation for the VARIANT INFO 810 table. Similar pseudo-code can be applicable to map data to the VARIANT SAMPLE 820 table. The differences are that the separators, as can be seen in VCF file 400 and the value strings are not in key/value format, rather an extra column "FORMAT" column specifies how to interpret the value strings for all the samples in the line.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (sometimes referred to as a computer program product) refers to physically embodied apparatus and/or device, such as for example magnetic discs, optical disks, memory, and Programmable Logic Devices (PLDs), used to provide machine instructions and/or data to a programmable data processor, including a machine-readable medium that receives machine instructions as a machine-readable signal. The term "machine-readable signal" refers to any signal used to provide machine instructions and/or data to a programmable data processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. For example, the current subject matter can be implemented using row store disk databases. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A computer implemented method comprising:
   receiving data comprising a text file, the text file being arranged in an extensible format and comprising a plurality of metadata lines, a header line, and a plurality of content lines;
   generating, based at least on metadata from the metadata lines, a plurality of metadata tables in a database, the plurality of metadata tables being formed according to a relational database schema, and the metadata from the plurality of metadata lines being mapped, based at least on prefix parameters from each metadata line, to the plurality of metadata tables;
   generating, based at least on content from the content lines, a plurality of content tables in the database, the plurality of content tables being formed according to the relational database schema, the content from the plurality of content lines being mapped, based at least on the header line, to the plurality of content tables, a first table of the plurality of content tables having a static structure that includes a fixed number of columns for storing content lines mapped to the first table, a second table of the plurality of content tables having a dynamic structure that enables an addition of at least one new column during runtime, the at least one new column accommodating an additional field in data received subsequent to the generation of the plurality of content tables; and
   performing, based at least on the plurality of metadata tables and/or the plurality of content tables, a database operation with respect to the data comprising the text file, the performance of the database operation comprising adding, to the second table, the at least one new column, the performance of the database operation further comprising generating a corresponding entry in a database log, the database log being used during a recovery to replay one or more operations performed on the data comprising the text file since a last savepoint.

2. The method of claim 1, wherein the mapping of the content from the content lines to the plurality of content tables comprises mapping gene sequence variations to corresponding reference genome position where the gene sequence variations occur.

3. The method of claim 1, wherein the text file is arranged according to the genomic variant call format.

4. The method of claim 1, wherein the generating of the plurality of metadata tables comprises the prefix parameters determining at least one of a metadata table name, number of columns and data types for the columns.

5. The method of claim 1, wherein the mapping of the metadata from the metadata lines to the plurality of metadata tables comprises:
   identifying key-value pairs from each metadata line;
   storing contents from metadata lines that contain only one key-value pair in single key-value pair metadata tables comprising a single column for the keys from all the metadata lines and a corresponding column for values from all the metadata lines; and
   storing contents from metadata lines that contain multiple key-value pairs in multiple key-value pair metadata tables comprising a column for each unique key, wherein the column is named after the key, and wherein the corresponding values are mapped into the rows of the columns named after the keys.

6. The method of claim 1, wherein the mapping of the content from the content lines to the plurality of content tables comprises:
   identifying header parameters from the header line; and
   generating content tables with the header parameters from the header line defining the content tables names within the relational database;

wherein each content table comprises at least a column storing contents associated with the header parameter defining the name of the content table.

7. The method of claim 6, further comprising:
determining that the header parameter has more than one corresponding value; and generating, in the content table, an additional row under the header parameter for each corresponding value, and incrementing a record count by one with each additional row.

8. The method of claim 6, wherein the header parameters from the header line comprise at least one of a position, identification, alternate, quality and filter parameter.

9. The method of claim 6, wherein an alternates content table stores reference alleles and corresponding alternate alleles, wherein the alternates content table comprises at least one column storing both the reference allele and corresponding alternate allele at a particular chromosome position, wherein each reference allele and corresponding alternate alleles at a particular chromosome position are mapped into separate rows in the column, wherein a record count value increments by one with each additional row, and wherein an index number, starting at zero to represent the reference allele increments by one for each alternate allele mapped into each additional row, and wherein the alternate content table includes an allele length column.

10. The method of claim 1, wherein the database comprises a columnar data store storing database tables as sections of columns.

11. The method of claim 1, wherein the database is an in-memory database storing the metadata tables and the content tables in main memory.

12. The method of claim 1, further comprising:
generating a lookup table, the lookup table providing a mapping between the at least one new column and the keys.

13. A non-transitory computer program product storing instructions which, when executed by at least one data processor forming part of at least one computing system, result in operations comprising:
receiving data comprising a text file, the text file being arranged in an extensible format and comprising a plurality of metadata lines, a header line, and a plurality of content lines;
generating, based at least on metadata from the metadata lines, a plurality of metadata tables in a database, the plurality of metadata tables being formed according to a relational database schema, and the metadata from the plurality of metadata lines being mapped, based at least on prefix parameters from each metadata line, to the plurality of metadata tables;
generating, based at least on content from the content lines, a plurality of content tables in the database, the plurality of content tables being formed according to the relational database schema, the content from the plurality of content lines being mapped, based at least on the header line, to the plurality of content tables, a first table of the plurality of content tables having a static structure that includes a fixed number of columns for storing content lines mapped to the first table, a second table of the plurality of content tables having a dynamic structure that enables an addition of at least one new column during runtime, the at least one new column accommodating an additional field in data received subsequent to the generation of the plurality of content tables; and
performing, based at least on the plurality of metadata tables and/or the plurality of content tables, a database operation with respect to the data comprising the text file, the performance of the database operation comprising adding, to the second table, the at least one new column, the performance of the database operation further comprising generating a corresponding entry in a database log, the database log being used during a recovery to replay one or more operations performed on the data comprising the text file since a last savepoint.

14. The non-transitory computer program product as in claim 13, wherein the mapping of the content from the content lines to the plurality of content tables comprises mapping gene sequence variations to corresponding reference genome position where the gene sequence variations occur.

15. The non-transitory computer program product as in claim 13, wherein the text file is arranged according to the genomic variant call format.

16. The non-transitory computer program product as in claim 13, wherein the generating of the plurality of metadata tables comprises the prefix parameters determining at least one of a metadata table name, number of columns and data types for the columns.

17. The non-transitory computer program product as in claim 13, wherein the mapping of the metadata from the metadata lines to the plurality of metadata tables comprises:
identifying key-value pairs from each metadata line;
storing contents from metadata lines that contain only one key-value pair in single key-value pair metadata tables comprising a single column for the keys from all the metadata lines and a corresponding column for values from all the metadata lines; and
storing contents from metadata lines that contain multiple key-value pairs in multiple key-value pair metadata tables comprising a column for each unique key, wherein the column is named after the key, and wherein the corresponding values are mapped into the rows of the columns named after the keys.

18. The non-transitory computer program product as in claim 13, wherein the mapping of the content from the content lines to the plurality of content tables comprises:
identifying header parameters from the header line; and
generating content tables with the header parameters from the header line defining the content tables names within the relational database;
wherein each content table comprises at least a column storing contents associated with the header parameter defining the name of the content table.

19. The non-transitory computer program product as in claim 18, further comprising:
determining that the header parameter has more than one corresponding value; and generating, in the content table, an additional row under the header parameter for each corresponding value, and incrementing a record count by one with each additional row.

20. The non-transitory computer program product as in claim 18, wherein an alternates content table stores reference alleles and corresponding alternate alleles, wherein the alternates content table comprises at least one column storing both the reference allele and corresponding alternate allele at a particular chromosome position, wherein each reference allele and corresponding alternate alleles at a particular chromosome position are mapped into separate rows in the column, wherein a record count value increments by one with each additional row, and wherein an index number, starting at zero to represent the reference allele increments by one for each alternate allele mapped into each additional row, and wherein the alternate content table includes an allele length column.

21. A system comprising:
at least one data processor; and
at least one memory storing instructions which, when executed by the at least one data processor, result in operations comprising:
receiving data comprising a text file, the text file being arranged in an extensible format and comprising a plurality of metadata lines, a header line, and a plurality of content line;
generating, based at least on metadata from the metadata lines, a plurality of metadata tables in a database, the plurality of metadata tables being formed according to a relational database schema, and the metadata from the plurality of metadata lines being mapped, based at least on prefix parameters from each metadata line, to the plurality of metadata tables;
generating, based at least on content from the content lines, a plurality of content tables in the database, the plurality of content tables being formed according to the relational database schema, the content from the plurality of content lines being mapped, based at least on the header line, to the plurality of content tables, a first table of the plurality of content tables having a static structure that includes a fixed number of columns for storing content lines mapped to the first table, a second table of the plurality of content tables having a dynamic structure that enables an addition of at least one new column during runtime, the at least one new column accommodating an additional field in data received subsequent to the generation of the plurality of content tables; and
performing, based at least on the plurality of metadata tables and/or the plurality of content tables, a database operation with respect to the data comprising the text file, the performance of the database operation comprising adding, to the second table, the at least one new column, the performance of the database operation further comprising generating a corresponding entry in a database log, the database log being used during a recovery to replay one or more operations performed on the data comprising the text file since a last savepoint.

* * * * *